United States Patent [19]

Nunez

[11] Patent Number: 4,874,384
[45] Date of Patent: Oct. 17, 1989

[54] NEEDLE SAFETY GUARD

[75] Inventor: Chris E. Nunez, Garden Grove, Calif.

[73] Assignee: International Medical Innovators, Inc., San Clemente, Calif.

[21] Appl. No.: 72,665

[22] Filed: Jul. 13, 1987

[51] Int. Cl.⁴ .............................................. A61M 5/32
[52] U.S. Cl. ..................................... 604/198; 604/263; 128/919
[58] Field of Search .............................. 604/192–198, 604/160, 162, 165, 166, 110, 117, 243, 263; 128/329 A

[56] References Cited

U.S. PATENT DOCUMENTS

| | | | |
|---|---|---|---|
| 1,373,669 | 4/1921 | Pittenger | 604/192 |
| 2,571,653 | 10/1951 | Bastien | 128/218 |
| 2,592,744 | 4/1952 | Jagger et al. | 604/192 |
| 2,847,995 | 8/1958 | Adams | 128/214 |
| 2,847,996 | 8/1958 | Cohen | 128/218 |
| 2,888,923 | 6/1959 | De Cunha Reis | 128/218 |
| 2,894,509 | 7/1959 | Bednarz | 604/192 |
| 3,306,290 | 2/1967 | Weltman | 128/218 |
| 3,306,291 | 2/1967 | Burke | 128/218 |
| 3,356,089 | 12/1967 | Francis | 128/221 |
| 3,485,239 | 12/1969 | Vanderbeck | 128/218 |
| 3,780,734 | 12/1973 | Wulff | 128/218 |
| 3,809,095 | 5/1974 | Cimber | 604/162 |
| 3,884,230 | 5/1975 | Wulff | 128/221 |
| 3,889,673 | 6/1975 | Dovey et al. | 604/192 |
| 3,890,971 | 6/1975 | Leeson | 128/218 |
| 3,905,375 | 9/1975 | Toyama | 128/329 A |
| 4,139,009 | 2/1979 | Alvarez | 128/218 |
| 4,232,669 | 11/1980 | Nitshke | 604/192 |
| 4,266,543 | 5/1981 | Blum | 128/218 |
| 4,266,544 | 5/1981 | Wardlaw | 128/218 |
| 4,273,123 | 6/1981 | Lemelson | 128/218 |
| 4,356,822 | 12/1982 | Winstead-Hall | 128/215 |
| 4,373,526 | 2/1983 | Kling | 128/215 |
| 4,392,859 | 7/1983 | Dent | 604/198 |
| 4,425,120 | 1/1984 | Sampson et al. | 604/198 |
| 4,507,117 | 3/1985 | Vining et al. | 604/196 |
| 4,573,976 | 3/1986 | Sampson et al. | 604/198 |
| 4,631,057 | 12/1986 | Mitchell | 604/198 |
| 4,643,199 | 2/1987 | Jennings, Jr. | 128/763 |
| 4,659,330 | 4/1987 | Nelson et al. | 604/192 |
| 4,664,259 | 5/1987 | Landis | 206/365 |
| 4,675,005 | 6/1987 | Deluccia | 604/110 |
| 4,676,783 | 6/1987 | Jagger et al. | 604/171 |
| 4,702,739 | 10/1987 | Milorad | 604/198 |
| 4,723,943 | 2/1988 | Spencer | 604/263 |

FOREIGN PATENT DOCUMENTS 123520  8/1916  United Kingdom ............... 604/165

Primary Examiner—Stephen C. Pellegrino
Assistant Examiner—Ralph Lewis
Attorney, Agent, or Firm—Stetina and Brunda

[57] ABSTRACT

A medical needle guard device is disclosed characterized by use of a pair of telescoping tubular sleeves mountable upon the hub of conventional medical needles by plural clip inserts positionable within one of the tubular sleeves. The plural clips may be specifically formed in differing configurations and positioned at differing axial positions along the length of one of the tubular sleeves to permit the medical needle guard to be retrofitted onto differing medical needle hubs.

6 Claims, 2 Drawing Sheets

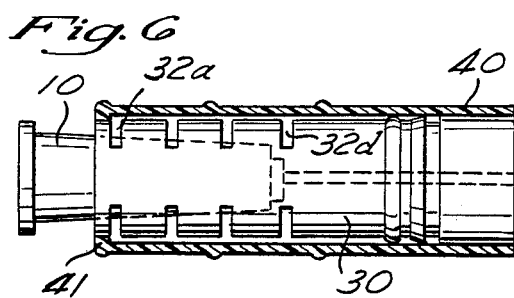
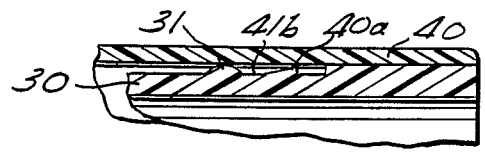
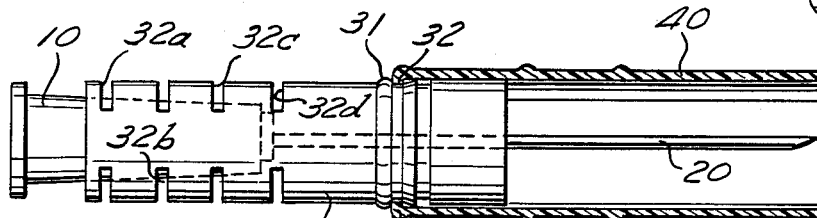
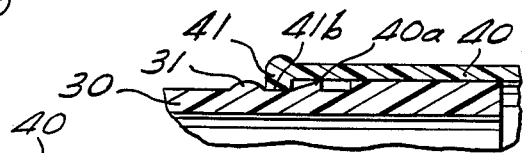
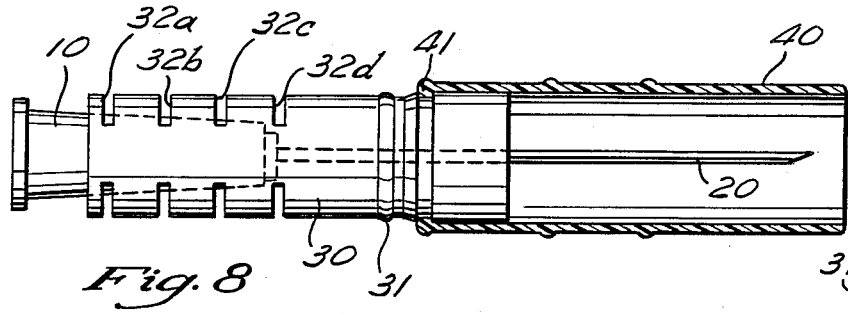
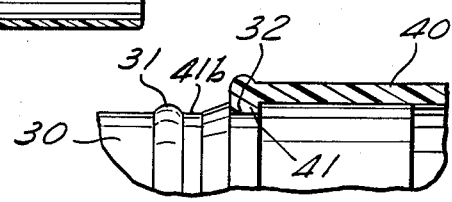
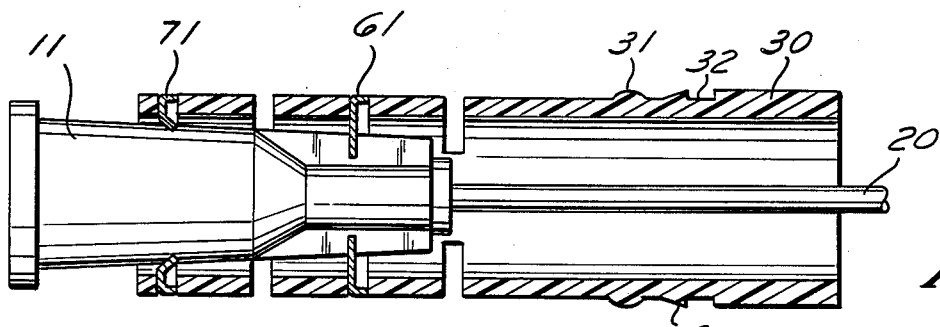
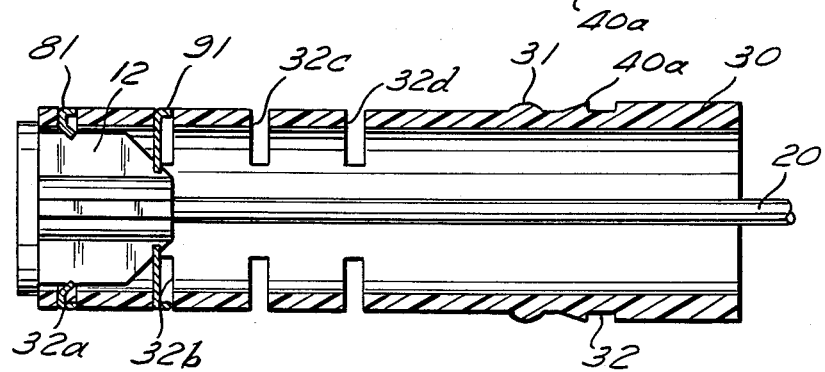

NEEDLE SAFETY GUARD

BACKGROUND OF THE INVENTION

1. Field of the Invention

The present invention concerns safety guards and retrofitting of safety guards to medical needles.

2. Description of the Relevant Art

Accidental needle stick injuries are common among health care workers such as doctors, nurses, laboratory personnel and housekeeping personnel. Accidental needle sticks with contaminated needles can result in the transmission of those diseases which ar transmissible through the blood. The severe health hazards and consequences associated with these diseases have resulted in well-thought-out protocols for handling medical needles and a near universal use of needle and syringe disposal containers.

Notwithstanding the care taken with contaminated medical needles, it is estimated in the publication *Bio-Medical International*, Vol. IX. 23-24 for December, 1986 that "an estimated 800,000 sharp or needle sticks occur each year in the U.S.". It is further estimated that "primary treatment (gamma globulin, hepatitis B immune globulin, tetanus) and subsequent blood analysis and care costs . . . $600-$1,000 per incident". This figure may be compared with a similar report that "each needle stick injury cost a hospital more than $200.00" as stated in U.S. Pat. No. 4,592,744. Whatsoever the actual stick injury, it is indisputable that each such injury is psychologically disconcerting to the health care worker receiving the injury.

Accidental needle sticks most often occur when a drawer of blood, or any administrator injecting a patient, attempts to recap or dispose of a needle, syringe or vacuum tube phlebotomy system after use. Although modern health care protocols seldom allow for any prolonged exposure of a contaminated needle upon a work surface, in some instances a contaminated needle is set upon a work surface by one person, normally the administrator, and is subsequently removed for disposal by another person, normally an assistant or nurse. During the course of this handling and interchange accidental self-sticks and sticks of other persons occasionally occur.

Although prior art needle guards and sheaths have been developed to help prevent accidental needle sticks, such prior art guards have been incompatible with, i.e. incapable of being fitted to, the various differing style existing medical needles and syringes. In this regard, *Bio-Medical International* estimates the size of the total U.S. disposable medical needle syringe market to be approximately $260,000,000. Of this total market, approximately $132,000,000 is in the hospital segment. In this segment market leaders such Becton-Dickinson and Sherwood each possess an approximate 45 percent market share. In the physcan and consumer market segment, estimated at $73,000,000, Becton-Dickinson enjoys an approximate 70 percent market share. Finally, in the specialty market segment of approximate $55,000,000 Becton-Dickinson possesses an approximate 30 percent market share. while Sherwood possesses an approximate 20 percent market share. From these statistics it is obvious that any guard for a medical needle needs to be compatible with, i.e. retrofitable to, the various differing leading needle and syringe designs of manufacturers such as Becton- Dickinson and Sherwood.

If the fitting or the retrofitting of safety guards or sheaths to preexisting medical needles and/or syringes is to be contemplated, then certain properties of these medical needles and/or syringes should be considered. The tips of medical needles or syringes are extremely sharp, and should not be dulled by contact with any other surfaces prior to their use in medical injection. Medical needles and syringes are delivered into use in sterile condition, and must be maintained or reestablished in this condition after the fitting or retrofitting of any sheath thereon. Medical needles and syringes are preferably disposable, dictating that any retrofitted sheath should additionally be disposable. Particularly, such a sheath should be of low cost and should be no more environmentally hazardous than are the spent needles and syringes themselves.

In order to reliably and invariably perform its function, a guard or sheath should be permanently affixed to the medical needle and/or syringe which it protects. Despite variations in the physical structure of such needles and/or syringes, it would be useful if a protective sheath, nonetheless to the requiredment that it should be permanently affixed, were to be of universal application among and between the various prior art differing needles and syringes.

SUMMARY OF THE INVENTION

The present invention is specifically directed to the fitting and to the retrofitting of a guard or sheath onto existing medical needles and/or syringes of diverse types, i.e. structural configurations. A particular preferred guard disclosed herein comprises two tubular members which telescope relative to one another. A proximal end region of a first tubular member is formed to accomodate and be permanently affixed to the hub of differing medical needles or syringes and extends coaxially about the needle from this hub. The second tubular sleeve telescopes relative the first tubular sleeve from a retracted position wherein the tip of the medical needle or syringe is exposed to a locked and extended position wherein the tip of the needle is shielded from accidental contact.

In accordance with the present invention, a method and an apparatus by which sliding tubular sleeves of a universal standard configuration may be affixed to diverse types of medical needles and syringes, particularly exhibiting different hubs, is provided. In accordance with the invention, the first tubular sleeve of universal configuration carries and retains customized inserts within its bore at its proximal end region. The customized inserts are sized and adapted to frictionally engage the particular configuration and size of the hub which is associated with the particular type of the medical needle and syringe. The inserts preferably comprise clips which are spaced axially along the proximal end region of the first tubular sleeve. The clips are preferably formed in the shape of internal tooth lock washers. A first clip, i.e. retainer clip, frictionally engages the hub for retention of the sleeve thereon. A second clip, axially spaced from the first clip at a second distal position, stabilizes the first tubular sleeve in a coaxial position about the hub and the needle. Each of the two clips is customized in the size and shape of its interior aperture either to frictionally engage for purposes of retention or to abut for purposes of stabilization a particular hub of a particular type of medical needle or syringe.

Further, in accordance with the present invention, the inserts retained and carried by the first tubular sleeve are preferably formed so as to be interlocked with complementary slotted apertured features within the bore of the first tubular sleeve. A multiplicity of these features are repeated as an array axially along the proximal end region of the first sleeve. The retainer inserts are interlocked with selected ones of the array of features. The inserts are thereby retained within the tubular sleeve at certain pre-selected locations axially along the sleeve. These locations, and the inserts which interlock the sleeve to the hub thereat, have a preselected displacement along the tubular sleeve and a preselected distance of separation. This preselected displacement and distance of separation places the customized inserts at appropriate positions so as to enable the first tubular member to universally engage any one particular hub which is associated with a particular type medical needle or syringe. Thus the use of particularly sized, configured, separated and positioned (along both the first tubular sleeve and the hub) retainer inserts permits a tubular sleeve of universal configuration to be adaptively fitted to diverse hubs which are associated with diverse types of medical needles and syringes.

The medical needle guard in accordance with the present invention is configured and assembled by positioning the first and second tubular members for reciprocal axial sliding and by inserting retainer inserts at selected positions axially along the proximal end region of the first sleeve. The particular retainer inserts selected; the particular positions within which these retainer inserts are inserted; and the particular separation of these positions are all pre-selected in consideration of the particular hub associated with a particular type of medical needle or syringe which they will engage. Engagement of the hub is accomplished by sliding the first tubular member, with inserts affixed therein, onto the hub in the proximal direction. This assembly process is conducted without contact to the tip of the needle, and may be performed under sterile conditions.

BRIEF DESCRIPTION OF THE DRAWINGS

These as well as other features of the present invention will become more apparent upon reference to the drawings wherein:

FIG. 3 is a side view, partially in cross-section, of the first preferred embodiment of a needle guard apparatus in accordance with the present invention.

FIG. 6 is a side view, partially in cross-section, showing the retracted position of the first preferred embodiment of a needle guard apparatus in accordance with the present invention.

FIG. 6a is a detailed cross-sectional view showing the preferred manner of sliding contact between the tubular members within the first preferred embodiment when such members are in the retracted position.

FIG. 7 is a side view, partially in cross-section, showing the initial, first detent position of the tubular members within the first preferred embodiment.

FIG. 7a is a detail cross-sectional view showing the manner of sliding contact between the tubular members of the preferred embodiment at the first detent position.

FIG. 8 is a side view, partially in cross-section, showing the final, second detent position assumed by the tubular members of the first preferred embodiment.

FIG. 8a is a detail cross-sectional view showing the manner of sliding engagement between the first and the second tubular members of the first preferred embodiment at the second detent position.

FIG. 9 is a side view, partially in cross-section, showing a second preferred embodiment of a needle guard apparatus in accordance with the present invention.

FIG. 10 is a side view, partially in cross-section, showing a third preferred embodiment of a needle guard apparatus in accordance with the present invention.

DESCRIPTION OF THE PREFERRED EMBODIMENT

Figure 1:
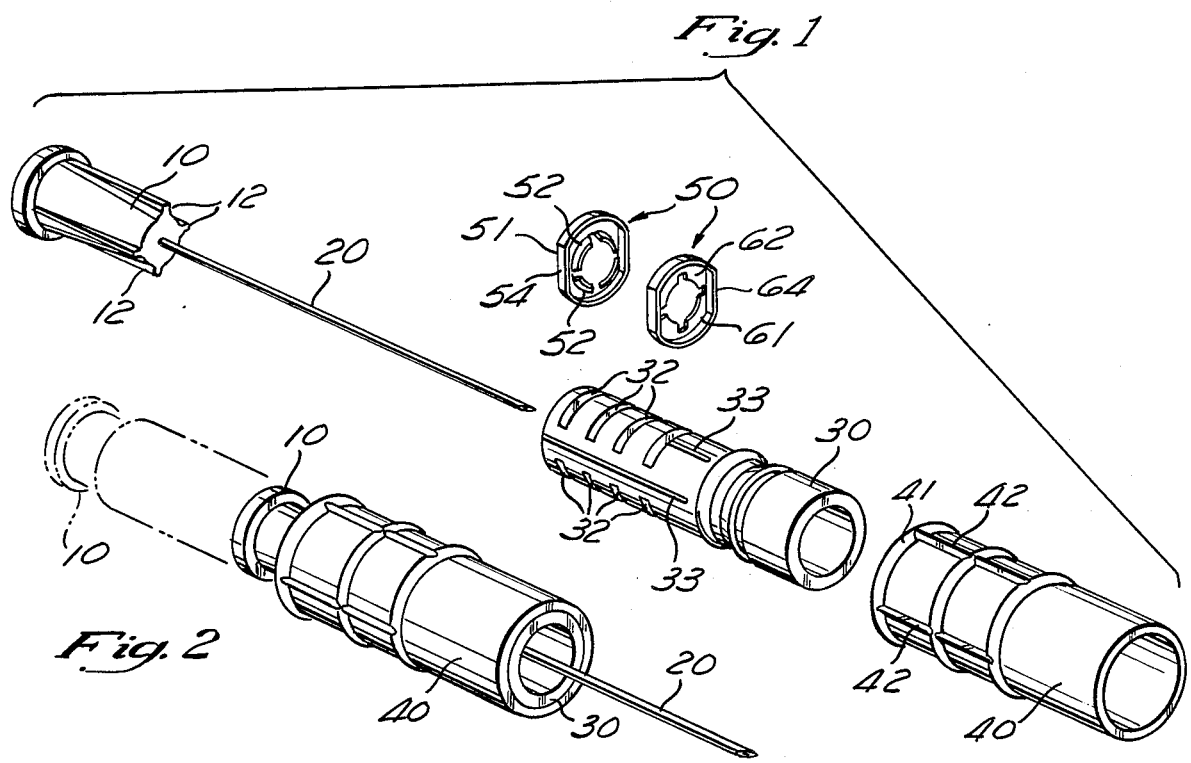
FIG. 1 is an exploded perspective view depicting in diagrammatic form a first preferred embodiment of a needle guard apparatus in accordance with the present invention.
Figure 2:
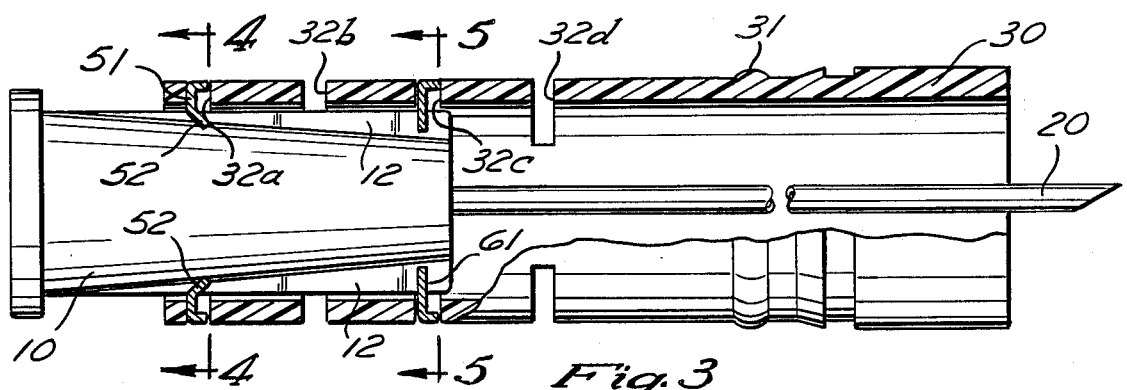
FIG. 2 is a perspective view depicting the operation of the first preferred embodiment which was previously shown in FIG. 1.

The present invention concerns the fitting and the retrofitting of safety guards or sheaths to medical needles and syringes. A first preferred embodiment apparatus in accordance with the present invention is generally shown in FIGS. 1–8a. The guard, which may essentially comprise any hollow structure capable of receiving the needle and extending throughout its length, is shown within FIG. 1 to preferably consist of a first tubular sleeve 30 and a second tubular sleeve 40. The sleeves 30 are preferably formed of medical grade polyvinylchloride (PVC) material, however, other conventional medical grade materials are contemplated. The first tubular sleeve 30 is adapted to be affixed at its proximal end region to the hub 10 of a conventional medical needle or syringe 20. In this mounted and affixed position, the first tubular sleeve 30 does not extend axially along the entire length of needle 20, but rather, only along a portion thereof, leaving an adequate length of the needle 20 exposed (as is illustrated in FIG. 2) so as to permit the use of needle 20 for medical injection purposes.

The second tubular sleeve 40 is movably mounted to the sleeve 30 to axially telescope relative to first tubular sleeve 30 from an initial distal position, assumed when the apparatus is delivered into use and illustrated in FIG. 7, to a retracted proximal position which is illustrated in FIG. 2 and FIG. 6. After use and contamination of the needle 20, the second tubular sleeve 40 may be telescoped in the distal direction along tubular sleeve 30 to its final distal position which is illustrated in FIG. 8. In this final position the entire length of the needle 20 is sheathed, thereby insuring against any accidental needle sticks by a user or patient.

The sleeves 30, 40 are preferably prevented from rotation relative to one another during their bi-directional telescoping motion by plural axial ridges 33 symetrically spaced upon the exterior surface of inner tubular sleeve 30. These ridges 33 engage complementary shaped axial grooves 41 formed on the interior surface of outer tubular sleeve 40. The locations of the complementary ridges and grooves could obviously be reversed. The sleeves 30, 40 need not be prevented from rotation relative to one another and relative to the needle hub 10 to which the sleeves will be affixed (in a manner to be explained) in order to realize the advantages of the present invention. However, the positive control of rotation helps to permit positive and precise control of the needle and needle guard apparatus by the medical user and is therefore preferred.

The two tubular elements 30 and 40, and the manner of their bi-directional sliding and telescoping relationship constitute but one aspect of the present invention. Indeed, the needle guard or sheath which preferably comprises two tubular sleeve elements sliding relative to one another could instead be constructed of but a single, unitary tubular element. This alternative, unitary form of a needle guard might optionally be frangible, or otherwise severable, along its length and might further optionally be rejoinable along sliding axial surfaces, such as by screw threads or otherwise. As still a further alternative, a needle guard might comprise more than two tubular members. These members might twist or screw relative to one another as well as slide or telescope. Therefore, the detailed nature of the needle guard which is affixed coaxially with and along the length of medical needle 20 will be recognized to potentially be of diverse forms. These diverse forms are still within the scope and spirit of the present invention for affixing a guard about a pre-existing medical needle.

In accordance with the present invention, a needle guard of universal configuration may be fitted, adapted and affixed to hubs of various lengths, diameters and configurations. These hubs of differing configuration are respectively associated with conventional medical needles and syringes of diverse types and manufacturers. Particularly, the hub 10 illustrated in FIGS. 1-5 comprises a hub of a conventional Sherwood standard needle. The sleeve 30 of the needle guard of the present invention is formed to include a central axial bore extending throughout its length, sized to have a diameter greater than the effective diameter of the hubs of various manufactures to permit the sleeve to extend thereover. The sleeve 30 is additionally tailored to be mounted upon the particular hub 10 by plural inserts 50, which particular inserts 51 and 61 are shown in FIG. 1. These inserts 50 are inserted within the interior bore of the first tubular sleeve 30 and are retained therein by engagement with complementary features formed upon the sleeve 30. These features could comprise ridges, grooves or any of innumerable types of protrusions or indentations. However, preferably they comprise plural slotted apertures 32, axially spaced along the length of the sleeve 30 sized to frictionally engage and capture one or more inserts 50 therein. In this regard, the width of the slotted apertures 32 is sized to be slightly less than the width of the inserts 50 to permit their frictional insertion and coaxial maintenance within the interior of the sleeve 30.

In FIG. 3 it is shown that a first, proximal retainer insert 51 is disposed within slotted apertures 32a of tubular sleeve 30 by being slid into position before the needle hub 10 or needle 20 is positioned within the tubular sleeve 30. A second, distal stabilizer insert 61 is similarly slid into slotted aperture 32c of tubular sleeve 30. The apertures 32b and 32d to tubular sleeve 30 are not used in the adaptation of the universal needle safety guard to the particular Sherwood standard needle hub 10 that is illustrated in FIGS. 1-5, but as will be recognized infra, are utilized in applications of other conventional needle hub configurations.

Figure 4:
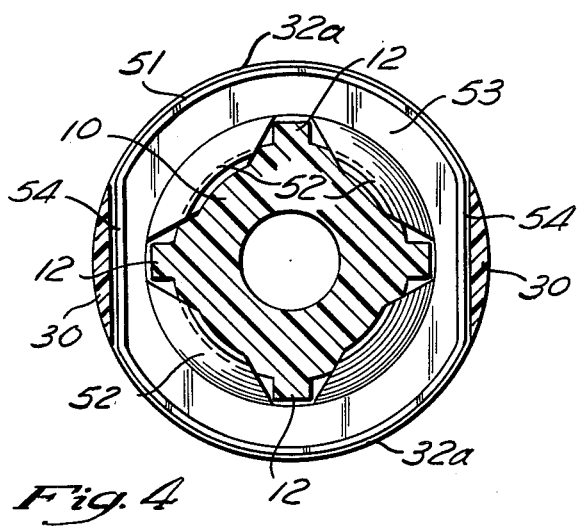
FIG. 4 is a cross-sectional view taken along aspect line 4—4 shown in FIG. 3, showing a retainer clip insert used within the first preferred embodiment.

A cross-sectional view of retainer insert 51 taken along aspect line 4—4 (shown in FIG. 3) is shown in FIG. 4. The retainer insert or clip 51 is particularly configured and adapted for frictional engagement with the hub 10 in order to securely mount the first tubular sleeve 30 permanently thereon. It is preferably fabricated of stainless steel and formed in a configuration analogous to an internal tooth lockwasher having an annular peripheral ring portion 53 with integral radially extending plural internal teeth 52. The plural teeth 52 all extend angularly radially inward (as best shown in FIG. 1 and 3), i.e. toward the distal end of hub 10 to facilitate initial axial sliding onto the hub and thereafter inhibit or resist axial sliding off of the hub in the opposite direction. As will be recognized, any axial sliding in this opposite direction, off of the hub, is resisted by wedging action of the teeth against the hub. The plural teeth are both appropriate in number (herein four) and are appropriately sized and disposed so as to engage in a complementary fashion to the precise configuration of the particular needle hub 10. More particularly, the plural teeth of retainer 51 frictionally engage the Sherwood standard needle hub 10, while plural V-shaped voids or recesses are formed between the plural teeth 52 which receive plural raised flanges 12 formed on hub 10.

The stabilizer insert 61, which is axially spaced from the first retainer insert 51, is similarly formed having a generally complementary internal aperture configuration to the external configuration of the hub 10.

In this regard, the insert 51 does not preferably frictionally engage the hub. Rather, its function is primarily to stabilize the sleeve 30 upon the hub 10 in a substantially tilting or canting of the sleeve 30 thereupon.

Figure 5:
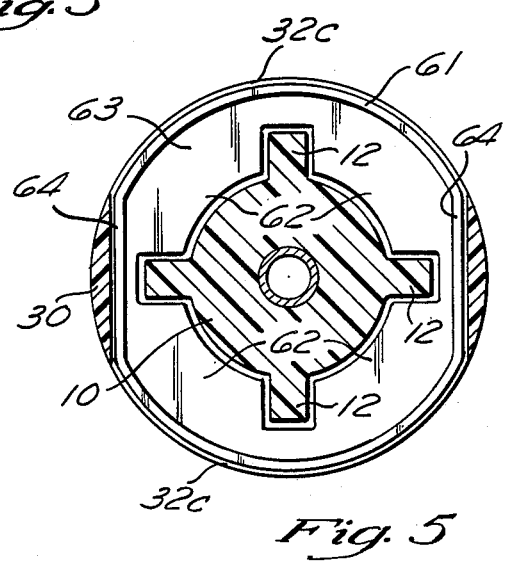
FIG. 5 is a cross-sectional view taken along aspect line 5—5 shown in FIG. 3, showing a stabilizer clip insert used within the first preferred embodiment.

The stabilizer insert 61 or clip is preferably formed having an annular ring portion 63 including a raised peripheral flange and plural internal projections or teeth 62 as shown in FIG. 5. The plural teeth 62 are adapted in numbers, size and contour to extend over and generally abut the hub 10 at their particular axial location upon such hub 10. As will be recognized, both inserts 51 and 61 include peripheral flats 54 and 64 respectively, which register the inserts relative the sleeve 30 and hub 10.

The universal needle guard in accordance with the present invention is specifically designed to be adapted to differing needle hubs merely by utilizing differing retainer and stabilizer inserts within appropriate slotted apertures 32 formed in the tubular sleeve 30. Exemplary thereof, the needle guard is further shown to be adapted to a standard Becton-Dickinson needle hub and to a Becton-Dickinson Vacutainer TM needle hub, respectively in FIGS. 9 and 10. The regular hub 11 (shown in FIG. 9) to the Becton-Dickinson standard needle is retained within the first tubular sleeve 30 by a first retainer insert or clip 71. In this regard, both retainer inserts 71 and 81 are formed having an internal aperture configuration complementary to the external configuration of their respective hubs so as to frictionally engage the same. The hub 12 (shown in FIG. 10) to the Vacutainer TM Becton-Dickinson needle is sized and adapted to be retained within sleeve 30 by still another first retainer insert or clip 81 which is but minutely different than the retainer insert 71. The retainer inserts 71 and 81 are fabricated substantially identical to retainer clip 61 shown in FIG. 4. The interior diameter of retainer insert 71 is 0.200 inches, whereas the interior diameter of retainer insert 81 is 0.230 inches both measures ±/−0.005 inches. The precision adaptation of the retainer inserts 51, 71 and 81 which are preferably made of stainless steel can thus be appreciated.

Similarly to the fact that retainer clips 71 and 81 are very nearly identical, the second stabilizer insert 81 to the hub 11 of the Becton-Dickinson standard needle is identical to the stabilizer insert 61 which fits the hub 10 of the Sherwood standard needle, which retainer insert 61 was shown and described in detail view in FIG. 5. The second stabilizer insert 91 to the hub 12 of the Becton-Dickinson Vacutainer TM needle (shown in FIG. 10) is, despite its different location within the apertures 32a-32d, so nearly identical to that second retainer insert 61 which is shown in detail view in FIG. 5, that a separate description is not warranted. Essentially, the stabilizer inserts 61 and 91 differ minutely in the width of the grooves or recesses which receive the flanges 12 (shown in FIG. 5) formed upon both the Sherwood standard needle hub 10 (shown in FIG. 2) and the Becton-Dickinson Vacutainer TM needle hub 12 (shown in FIG. 10). The precise dimensions of either the first retainer inserts 51, 71, and 81 or of the second stabilizer inserts 61 and 91 are less important than the concept, in accordance with the present invention, that these customized inserts can be precisely formed and appropriately selected and arrayed along the particular hub of a corresponding particular medical needle so as to permit the adaptation of a needle guard of universal configuration to existing medical needles of diverse types.

The system in accordance with the present invention for the fitting and retrofitting of medical needles with a needle guard will thus be seen to offer flexible adaptability to needles and syringes of diverse types, modest tooling and inventory costs, inexpensive metal spring clip and molded plastic sleeve components which are economically and ecologically suitable for disposal and a manner of fitting and/or retrofitting the guard which preserves the needle's sharpness and sterile condition. Particularly, as regards this manner of fitting and/or retrofitting, a preferred method in accordance with the present invention contemplates mounting the retainer and stabilizer inserts within a proximal end region of the first tubular sleeve. The proximal end region of the first tubular sleeve 30 and inserts may then be slid axially in the proximal direction onto a hub of the medical needle until the retainer insert frictionally engages the hub and the stabilizer insert is positioned about the hub so as to rigidly mount the first tubular sleeve upon the hub. Subsequently, the second tubular sleeve may be attached by sliding proximally onto the first tubular sleeve's distal end region. In this coaxial position, the tubular sleeves are engaged for axial sliding motion relative to one another. It is, of course, possible to vary the order of the steps, particularly by fitting the two tubular sleeves together before the proximal end region of a one sleeve (which is nominally, but needs not be, the interior one) is engaged, by the inserts to the hub. As will be recognized, the entire mounting procedure may be accomplished without ever touching the needle tip and may be conducted under sterile conditions with sterile needle guard components.

The method of utilizing the needle guard is best depicted in FIGS. 6-8a. Initially, the tubular sleeve 40 is positioned upon the sleeve 30 as depicted in FIGS. 7 and 7a wherein an annular lip 41 formed on the end of the sleeve 40 resides within an annular recess 41b formed on the periphery of the sleeve 30. In this axial detent position, the tubular sleeve 40 barely extends beyond the distal end of the needle 20 to guard the same as required in packaging applications. When the needle/syringe is desired to be utilized, the sleeve 40 may be axially reciprocated toward the hub 10 to a position illustrated in FIG. 6a wherein the needle 20 is exposed for use. As will be recognized, this "in use" position is maintained by the annular flange 41 being disposed between an annular stop 40a and annular projection or rib 31 formed on the exterior of the sleeve 30. After use of the needle, the sleeve 40 may be axially reciprocated or slid outwardly to its final axial position illustrated in FIG. 8 wherein the end of the needle 20 is disposed within the interior of the sleeve 40. In this final position the sleeve 40 is locked in relationship to sleeve 30 by engagement of the annular lip 41 within a complementary shaped annular recess 32 formed in the tubular sleeve 30. Subsequently, the entire hub, needle and needle guard may be disposed in a biologically safe disposal facility.

In accordance with the preceding explanation, the present invention will be perceived to be susceptible to diverse implementations and embodiments. For example, the numbers of inserts may be varied to accomodate different hub configurations, the scope of the present invention should be determined in accordance with those three preferred embodiments within which the present invention has been taught.

What is claimed is:

1. A protective apparatus mountable to the hub of a medical needle for guarding a needle element projecting from the hub, the apparatus comprising:
    a tubular guard sized to receive therein a needle element of a medical needle and at least a portion of a hub of the medical needle and axially positionable upon the length of said needle element to extend over and to guard a tip of the needle element;
    a first and second clip spaced axially along the tubular guard and the hub which first and second clip are inserted into a slotted aperture formed in the tubular guard,
    the first clip, spaced from the needle element in a proximal direction along the hub, for frictionally engaging the hub to retain the tubular guard thereupon;
    the second clip, spaced closer to the needle element along the hub than the first clip, for stabilizing the tubular guard coaxially about the hub.

2. The medical needle protective apparatus according to claim 1 wherein the first clip comprises:
    an apertured clip encircling the hub and presenting projecting teeth angularly disposed to frictionally engage the hub;
    an apertured clip encircling the hub and presenting projecting tabs disposed to abut the hub to stabilize the tubular guard coaxially thereabout.

3. A method of fitting a guard onto a medical needle comprising:
    mounting plural inserts within an end region of a first tubular sleeve, which inserts constrict the internal diameter of the sleeve;
    sliding the end region of the first tubular sleeve and its inserts axially in a first direction onto a hub of a medical needle until at least one of the plural inserts frictionally engages the hub sufficiently to permanently mount the first tubular sleeve positioned thereupon;

attaching a second tubular sleeve to the first tubular sleeve's distal end region for axially reciprocally sliding relative to the first tubular sleeve;

defining a plurality of attachment points axially along the end region of the first tubular sleeve;

wherein said defining of plurality points additionally comprises:

creating a pllurality of slotted apertures axially along the end region of the first tubular sleeves;

wherein the mounting of plural inserts comprises mounting plural inserts into respective ones of the plurality of slotted apertures.

4. A method of fitting a guard onto a medical needle comprising:

mounting plural inserts within an end region of a first tubular sleeve which inserts constrict the internal diameter of the sleeve;

sliding the end region of the first tubular sleeve and its inserts axially in a first direction onto a hub of a medical needle until at least one of the plural inserts frictionally engages the hub sufficiently to permanently mount the first tubular sleeve positioned thereupon;

attaching a second tubular sleeve to the first tubular sleeve's distal end region for axially reciprocally sliding relative to the first tubular sleeve;

forming plural inserts substantially in the shape of an internal tooth lock washer;

wherein the teeth of the plural inserts constrict the internal diameter of the first tubular sleeve;

wherein at least one of the plural inserts frictionally engages the hub at its internal teeth.

5. An apparatus capable of being mounted to a hub of a medical needle in order to guard the tip of the medical needle, the apparatus comprising:

a first tubular sleeve;

engagement means, retained and carried by the first tubular sleeve, for frictionally engaging a hub of the medical needle in order to mount the first tubular sleeve coaxially thereupon; and a second tubular sleeve sliding from the first tubular sleeve to a sufficient extention so as to guard a tip of the medical needle, said engagement means comprising a clip insert formed substantially in the shape of an internal tooth lock washer.

6. The apparatus according to claim 5 wherein the engagement means comprises teeth formed on the clip insert sized to frictionally engage the hub of the medical needle.

* * * * *